(12) United States Patent
Yoshino et al.

(10) Patent No.: US 10,364,495 B2
(45) Date of Patent: Jul. 30, 2019

(54) METHOD FOR PRODUCING A THIN FILM

(71) Applicant: ADEKA CORPORATION, Tokyo (JP)

(72) Inventors: Tomoharu Yoshino, Tokyo (JP); Atsushi Sakurai, Tokyo (JP); Tsubasa Shiratori, Tokyo (JP); Masako Hatase, Tokyo (JP); Hiroyuki Uchiuzou, Tokyo (JP); Akihiro Nishida, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 15/483,110

(22) Filed: Apr. 10, 2017

(65) Prior Publication Data

US 2017/0211184 A1 Jul. 27, 2017

Related U.S. Application Data

(62) Division of application No. 14/434,139, filed as application No. PCT/JP2013/081711 on Nov. 26, 2013, now Pat. No. 9,663,538.

(30) Foreign Application Priority Data

Dec. 25, 2012 (JP) .................................. 2012-281457

(51) Int. Cl.
*C23C 16/44* (2006.01)
*C23C 16/455* (2006.01)
(Continued)

(52) U.S. Cl.
CPC ........ *C23C 16/45553* (2013.01); *C07F 5/069* (2013.01); *C23C 16/06* (2013.01); *C23C 16/403* (2013.01); *C23C 16/44* (2013.01)

(58) Field of Classification Search
CPC ..................................................... C07F 5/069
See application file for complete search history.

(56) References Cited

U.S. PATENT DOCUMENTS

2006/0257567 A1 11/2006 Peters et al.
2009/0203222 A1 8/2009 Dussarrat et al.
(Continued)

FOREIGN PATENT DOCUMENTS

| JP | 2007-320831 | 12/2007 |
| JP | 2009-173587 | 8/2009 |
| JP | 2012-007192 | 1/2012 |

OTHER PUBLICATIONS

International Search Report PCT/JP2013/081711 dated Jan. 21, 2014.
(Continued)

*Primary Examiner* — Joseph A Miller, Jr.
(74) *Attorney, Agent, or Firm* — Young & Thompson

(57) ABSTRACT

The present invention relates to an aluminum compound represented by general formula (I). The present invention also relates to a thin film-forming raw material that contains this aluminum compound. In general formula (I), $R^1$ and $R^2$ each independently denote a straight chain or branched alkyl group having 2-5 carbon atoms, and $R^3$ denotes a methyl group or ethyl group. It is preferable for $R^1$ and $R^2$ to be ethyl groups. This compound has a low melting point, exhibits satisfactory volatility, has high thermal stability, and is suitable for use as a raw material used to form a thin film by a CVD method.

4 Claims, 2 Drawing Sheets

(51) Int. Cl.
    *C07F 5/06*     (2006.01)
    *C23C 16/40*     (2006.01)
    *C23C 16/06*     (2006.01)

(56) References Cited

U.S. PATENT DOCUMENTS

2010/0247765 A1    9/2010   Yamada et al.
2013/0157475 A1*  6/2013   Thompson ........ H01L 21/02271
                                                          438/778

OTHER PUBLICATIONS

Sean T. Barry, Roy G. Gordon and Valerie A. Wagner, "Monomeric Chelated Amides of Aluminum and Gallium: Volatile, Miscible Liquid Precursors for CVD", Mat. Res. Soc. Symp. Proc., vol. 606 (2000), pp. 83-89.
Extended European Search Report—EP 13 86 9190—dated Aug. 17, 2016.
Vincenzo Passarelli et al: "Synthesis of 1-5 amino- and amino-aluminium derivatives and investigation of their dynamics in solution", Dalton Transactions: The International Journal for Inorganic, Organometallic and Bioinorganic Chemistry, No. 7, Mar. 24, 2003 (Mar. 24, 2003), pp. 1284-1291, XP055294084, GB ISSN: 1477-9226, DOI: 10.1039/b211720g.

* cited by examiner

[Fig. 1]
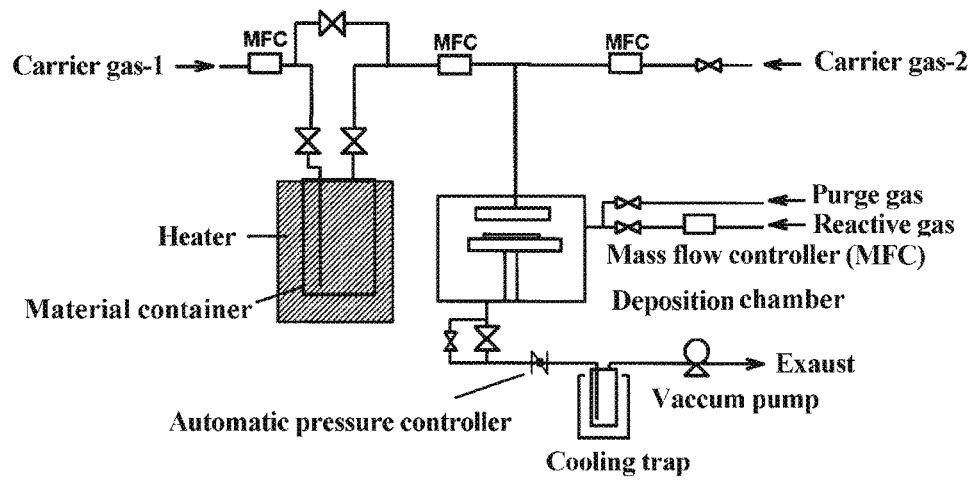
[Fig. 2]
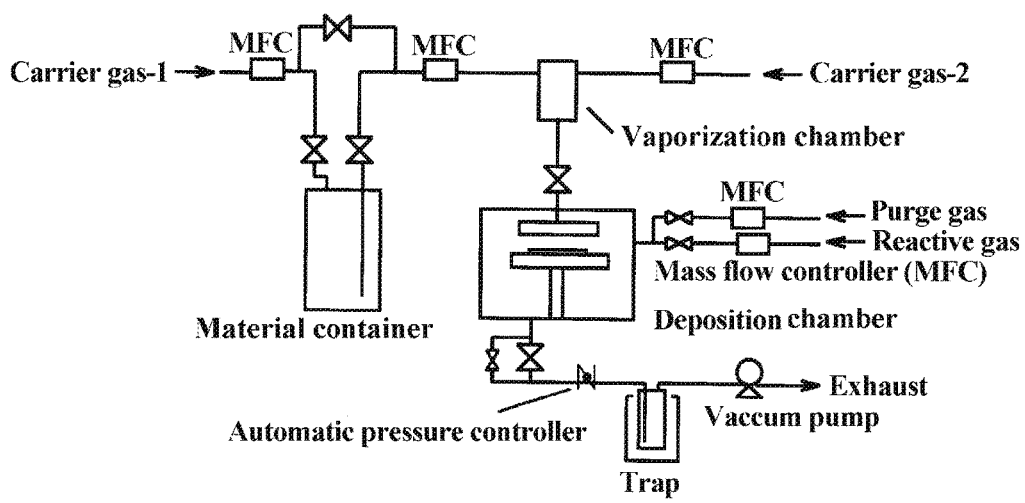

[Fig. 3]
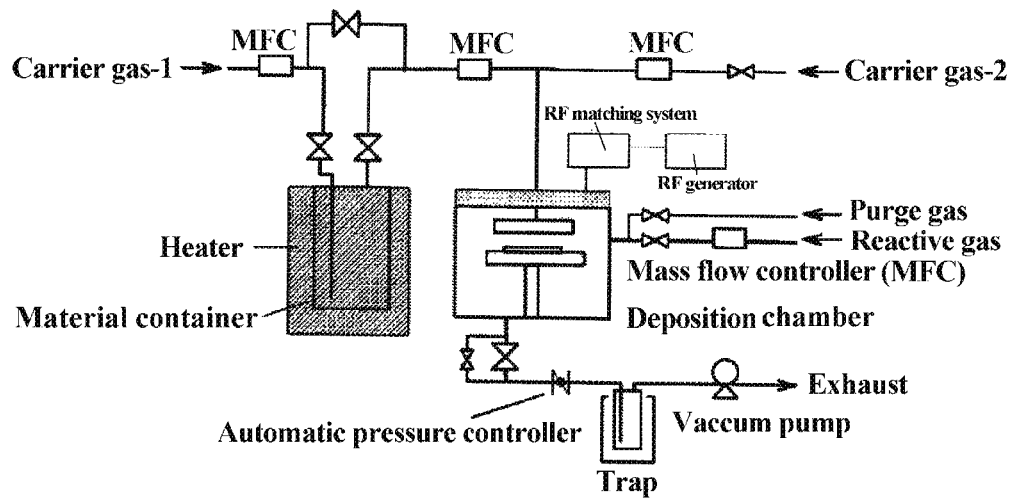
[Fig. 4]
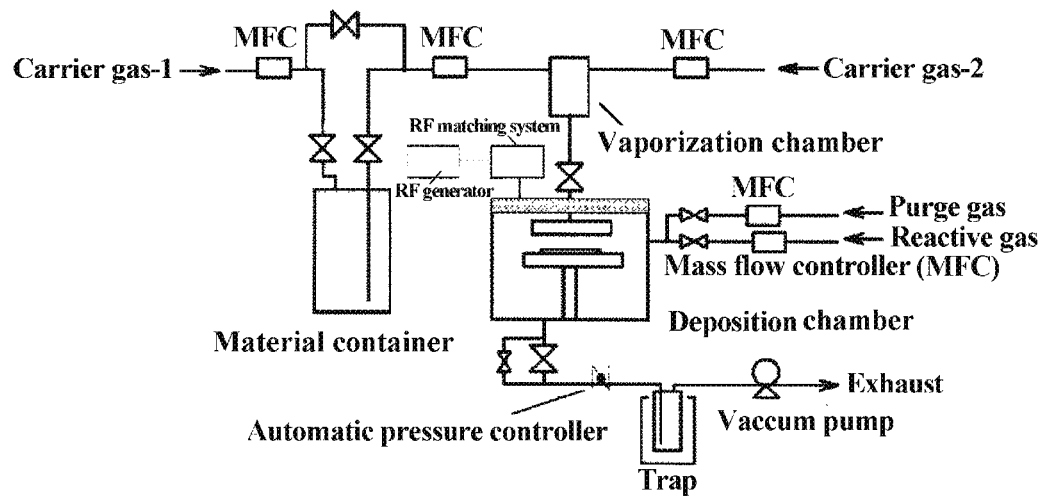

METHOD FOR PRODUCING A THIN FILM

TECHNICAL FIELD

This invention relates to a novel aluminum compound having a specific structure, a material for thin film formation containing the aluminum compound, and a process for forming an aluminum-containing thin film using the material.

BACKGROUND ART

An aluminum-containing thin film material exhibits specific electric and optical characteristics and has found wide applications. For example, an aluminum or aluminum alloy thin film has been used as an LSI wiring material for its high conductivity and electromigration resistance. An aluminum oxide based thin film has been used as a hardcoat of machine parts and tools; an insulator film, a gate insulator, and a dielectric film of semiconductor memories; electronic components, such as a hard disk MR head; and optical glass for optical communication circuits.

Processes for forming the above-described thin film include sputtering, ion plating, MOD techniques such as a dipping-pyrolysis process and a sol-gel process, and chemical vapor deposition techniques. Chemical vapor deposition techniques (hereinafter abbreviated as CVD) including atomic layer deposition (ALD) is the most suitable for many advantages, such as compositional controllability, excellent step coverage, suitability to large volume production, and capability of hybrid integration.

Various aluminum compounds are known as raw materials for CVD. For example, Patent Literature 1 below discloses trimethylaluminum and alkoxyalanes typified by a dimethylaluminum alkoxide compound as thin film forming materials but gives no mention of the aluminum compound of the invention. Patent Literature 1 reports that $AlMe_2$ (OiPr) is the most preferred thin film forming material out of the alkoxyalanes. However, $AlMe_2(OiPr)$ is not satisfactory as a material for chemical vapor deposition on account of its low thermal stability. Trimethylaluminum is not satisfactory either as a material for chemical vapor deposition because of its pyrophoricity. Non-patent Literature 1 below discloses an aluminum amide compound of formula $(Me_2NCH_2CH_2NMe)Al(NMe_2)_2$ but has no mention of the aluminum compound of the invention.

CITATION LIST

Patent Literature

Patent Literature 1: US 2009/203222A1

Non-Patent Literature

Non-patent Literature 1: Sean T. Barry, Roy G. Gordon & Valerie A. Wagner, "Monomeric Chelated Amides of Aluminum and Gallium: Volatile, Miscible Liquid Precursors for CVD", *Mat. Res. Soc. Symp. Proc.*, vol. 606 (2000), pp. 83-89

SUMMARY OF THE INVENTION

Technical Problem

Properties required of a compound (precursor) suited as a raw material for thin film formation involving vaporization of the compound, such as CVD, are a low melting temperature (to be transportable in liquid form), a low liquid viscosity, a high vapor pressure (vaporizability), and high thermal stability. For application to ALD, in particular, high thermal stability of a precursor is important because of the involvement of the step in which the precursor is vaporized by heat, and the vapor is transported to a substrate without being pyrolyzed, deposited on the substrates heated to a high temperature without being pyrolyzed, and then allowed to react with a reactive gas pulsed to the deposit. Any conventional aluminum compound fails to sufficiently meet these requirements.

Solution to Problem

As a result of extensive investigations, the inventor has found that the above problem is solved by an aluminum compound having a specific structure and reaches the present invention.

The invention provides an aluminum compound represented by general formula (I):

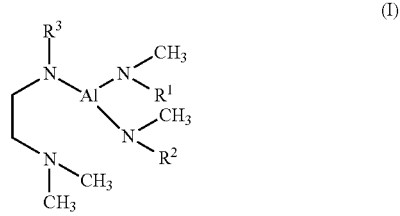

(I)

The invention also provides a material for thin film formation containing the aluminum compound of general formula (I).

The invention also provides a process for forming a thin film including vaporizing the material for thin film formation and introducing the resulting vapor containing the aluminum compound into a deposition chamber having a substrate placed therein to cause the aluminum compound to decompose and/or chemically react to form an aluminum-containing thin film on the substrate.

Effects of Invention

The invention provides an aluminum compound having a low melting point, sufficient volatility, and high thermal stability. The aluminum compound is suitable as a material for thin film formation by CVD.

BRIEF DESCRIPTION OF DRAWINGS

FIG. 1 is a schematic illustration of an example of an apparatus for chemical vapor deposition that can be used to carry out the process for forming an aluminum-containing thin film according to the invention.

FIG. 2 is a schematic illustration of another example of an apparatus for chemical vapor deposition that can be used to carry out the process for forming an aluminum-containing thin film according to the invention.

FIG. 3 is a schematic illustration of still another example of an apparatus for chemical vapor deposition that can be used to carry out the process for forming an aluminum-containing thin film according to the invention.

FIG. 4 is a schematic illustration of yet another example of an apparatus for chemical vapor deposition that can be used to carry out the process for forming an aluminum-containing thin film according to the invention.

DESCRIPTION OF EMBODIMENTS

The invention will be described in detail generally based on its preferred embodiments.

The aluminum compound of the invention is represented by general formula (I). It is suitable as a precursor used in thin film formation including a vaporization step, such as CVD. It is particularly suitable as a precursor for use in ALD because of its high thermal stability.

Examples of the C2-C5 straight or branched chain alkyl group as represented by $R^1$ and $R^2$ include ethyl, propyl, isopropyl, butyl, sec-butyl, tert-butyl, isobutyl, pentyl, sec-pentyl, tert-pentyl, isopentyl, and neopentyl. $R^3$ represents methyl or ethyl.

In the case where the compound of general formula (I) is used in a thin film formation process including the step of vaporizing the compound, $R^1$, $R^2$, and $R^3$ in formula (I) are preferably selected so that the compound is liquid and has a high vapor pressure at ambient temperature and ambient pressure. It is more preferred for the compound to have a low viscosity in its liquid state in terms of ease of transportation. Specifically, the compound in which $R^1$ and $R^2$ are each ethyl or isopropyl is liquid at ambient temperature and exhibits high thermal stability. Inter alia, the compound in which $R^1$ and $R^2$ are each ethyl, especially the compound in which $R^1$ and $R^2$ are each ethyl, and $R^3$ is methyl, is preferred for its low viscosity in a liquid state. In the case when the compound is used for an MOD process involving no vaporization step, $R^1$, $R^2$, and $R^3$ may be selected as appropriate to the solubility in a solved used, the thin film formation reaction, and the like.

Preferred examples of the aluminum compounds of the invention include, but are not limited to, compound No. 1 through 8 given below.

Compound No. 1
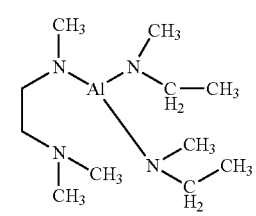

Compound No. 2
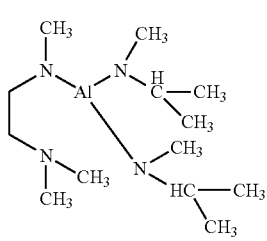

Compound No. 3
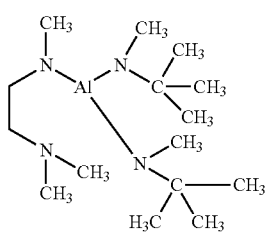

Compound No. 4
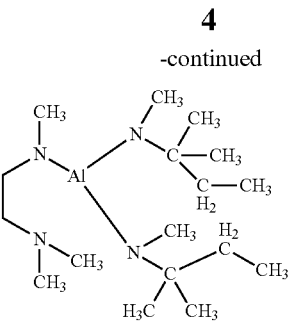

Compound No. 5
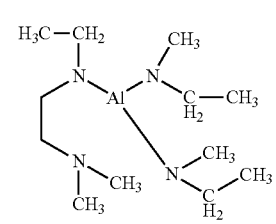

Compound No. 6
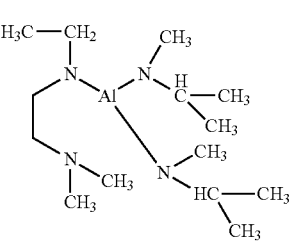

Compound No. 7
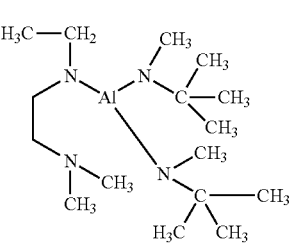

Compound No. 8
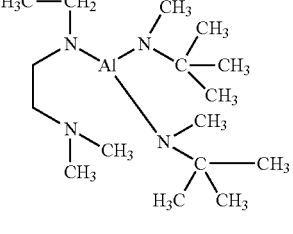

The aluminum compound of the invention is not limited by the method of preparation and may be prepared making use of known reactions. For example, the compound of the invention can be obtained by allowing an aluminum hydride to react with a dialkylamine the structure of which corresponds to the compound to be prepared and a diamine compound the structure of which corresponds to the compound to be prepared or by allowing aluminum chloride to react with a dialkylamine the structure of which corresponds to the compound to be prepared and a diamine compound the structure of which corresponds to the compound to be prepared.

The thin film forming material according to the invention comprises the aluminum compound of the invention as a thin film precursor and may have a form appropriate to the process to which the material is applied. For example, in forming a thin film containing aluminum as a sole metal, the thin film forming material of the invention can be free of a metal or semimetal compound other than the aluminum compound of the invention. In forming a thin film containing aluminum and a metal other than aluminum and/or a semimetal, the thin film forming material of the invention can contain, in addition to the aluminum compound of the invention, a compound containing the metal other than aluminum and/or a compound containing the semimetal (hereinafter inclusively referred to as (an)other precursor(s)). When the thin film forming material contains another precursor, the content of the other precursors in the material is preferably 0.01 to 10 mol, more preferably 0.1 to 5 mol, per mole of the aluminum compound of the invention. The thin film forming material of the invention may further contain an organic solvent and/or a nucleophilic reagent as will be described later.

Since the aluminum compound (precursor) of thin film forming material of the invention has physical properties suitable to CVD and ALD as previously discussed, the thin film forming material is particularly useful as a material for chemical vapor deposition (hereinafter also called a CVD material).

For use as a material for chemical vapor deposition, the thin film forming material of the invention may have a form selected as appropriate for the CVD system adopted, such as a source delivery system.

The source delivery system is exemplified by a vapor delivery system in which a CVD material is vaporized by heating and/or pressure reduction in a material container and introduced into a deposition chamber having a substrate placed therein, if desired, together with a carrier gas, e.g., argon, nitrogen or helium, and a liquid delivery system in which a CVD material is delivered in the form of a liquid or a solution to a vaporization chamber, where it is vaporized by heating and/or pressure reduction and then introduced to a deposition chamber (referred to also as "deposition reaction unit"). When applied to the vapor delivery system, the aluminum compound represented by general formula (I) per se can be the CVD material. In the case of the liquid delivery system, the aluminum compound represented by general formula (I) per se or a solution of the compound in an organic solvent can be the CVD material.

In a multi-component CVD process, the source delivery systems include a system in which a plurality of precursors are separately vaporized and delivered (hereinafter referred to as a single-source system) and a system in which a plurality of the precursors are previously mixed at a prescribed ratio, and the mixture is vaporized and delivered (hereinafter referred to as a cocktail-source system). In the case of the cocktail-source system, the CVD material may be a mixture or mixed solution containing the aluminum compound of the invention or a mixture or mixed solution containing the aluminum compound of the invention and other precursor(s).

The organic solvent that can be used in the CVD material is not particularly limited, and any widely known organic solvent may be used. Examples of useful organic solvents include acetic esters, such as ethyl acetate, butyl acetate, and methoxyethyl acetate; ethers, such as tetrahydrofuran, tetrahydropyran, ethylene glycol dimethyl ether, diethylene glycol dimethyl ether, triethylene glycol dimethyl ether, dibutyl ether, and dioxane; ketones, such as methyl butyl ketone, methyl isobutyl ketone, ethyl butyl ketone, dipropyl ketone, diisobutyl ketone, methyl amyl ketone, cyclohexanone, and methylcyclohexanone; hydrocarbons, such as hexane, cyclohexane, methylcyclohexane, dimethylcyclohexane, ethylcyclohexane, heptane, octane, toluene, and xylene; hydrocarbons having a cyano group, such as 1-cyanopropane, 1-cyanobutane, 1-cyanohexane, cyanocyclohexane, cyanobenzene, 1,3-dicyanopropane, 1,4-dicyanobutane, 1,6-dicyanohexane, 1,4-dicyanocyclohexane, and 1,4-dicyanobenzene; pyridine, and lutidine. A solvent or a mixture of solvents to be used is selected according to, for example, solubility of the solute and the boiling temperature or ignition temperature in relation to the working temperature. In using these organic solvents, the total concentration of the aluminum compound of the invention and the other precursor(s) in the organic solvent is preferably 0.01 to 2.0 mol/l, still preferably 0.05 to 1.0 mol/l.

The other precursors that can be used in combination with the aluminum compound of the invention in multi-component CVD are not particularly limited, and compounds known as precursors used in CVD materials are useful.

Examples of the other precursors include compounds formed between silicon or a metal except aluminum and at least one compound selected from the group consisting of organic coordinating compounds, such as alcohol compounds, glycol compounds, β-diketone compounds, cyclopentadiene compounds, and organic amine compounds. The metal species of the other precursors include magnesium, calcium, strontium, barium, titanium, zirconium, hafnium, vanadium, niobium, tantalum, manganese, iron, ruthenium, cobalt, rhodium, iridium, nickel, palladium, platinum, copper, silver, gold, zinc, gallium, indium, germanium, tin, lead, antimony, bismuth, yttrium, lanthanum, cerium, praseodymium, neodymium, promethium, samarium, europium, gadolinium, terbium, dysprosium, holmium, erbium, thulium, and ytterbium.

Examples of the alcohol compounds that can be used as an organic ligand of the other precursors include alkyl alcohols, such as methanol, ethanol, propanol, isopropyl alcohol, butanol, sec-butyl alcohol, isobutyl alcohol, tert-butyl alcohol, pentyl alcohol, isopentyl alcohol, and tert-pentyl alcohol; ether alcohols, such as 2-methoxyethanol, 2-ethoxyethanol, 2-butoxyethanol, 2-(2-methoxyethoxy)ethanol, 2-methoxy-1-methylethanol, 2-methoxy-1,1-dimethylethanol, 2-ethoxy-1,1-dimethylethanol, 2-isopropoxy-1,1-dimethylethanol, 2-butoxy-1,1-dimethylethanol, 2-(2-methoxyethoxy)-1,1-dimethylethanol, 2-propoxy-1,1-diethylethanol, 2-sec-butoxy-1,1-diethylethanol, and 3-methoxy-1,1-dimethylpropanol.

Examples of the glycol compounds include 1,2-ethanediol, 1,2-propanediol, 1,3-propanediol, 2,4-hexanediol, 2,2-dimethyl-1,3-propanediol, 2,2-diethyl-1,3-propanediol, 1,3-butanediol, 2,4-butanediol, 2,2-diethyl-1,3-butanediol, 2-ethyl-2-butyl-1,3-propanediol, 2,4-pentanediol, 2-methyl-1,3-propanediol, 2-methyl-2,4-pentanediol, 2,4-hexanediol, and 2,4-dimethyl-2,4-pentanediol.

Examples of the β-diketone compounds include alkyl-substituted β-ketones, such as acetylacetone, hexane-2,4-dione, 5-methylhexane-2,4-dione, heptane-2,4-dione, 2-methylheptane-3,5-dione, and 2,6-dimethylheptane-3,5-dione; fluoroalkyl-substituted β-diketones, such as 1,1,1-trifluoropentane-2,4-dione, 1,1,1-trifluoro-5,5-dimethylhexane-2,4-dione, 1,1,1,5,5,5-hexafluoropentane-2,4-dione, and 1,3-diperfluorohexylpropane-1,3-dione; and ether-substituted β-diketones, such as 1,1,5,5-tetramethyl-1-methoxyhexane-2,4-dione, 2,2,6,6-tetramethyl-1-methoxyheptane-3,5-dione, and 2,2,6,6-tetramethyl-1-(2-methoxyethoxy)heptane-3,5-dione.

Examples of the cyclopentadiene compounds include cyclopentadiene, methylcyclopentadiene, ethylcyclopentadiene, propylcyclopentadiene, isopropylcyclopentadiene, butylcyclopentadiene, sec-butylcyclopentadiene, isobutylcyclopentadiene, tert-butylcyclopentadiene, dimethylcyclopentadiene, and tetramethylcyclopentadiene. Examples of the organic amine compounds include methylamine, ethylamine, propylamine, isopropylamine, butylamine, sec-butylamine, tert-butylamine, isobutylamine, dimethylamine, diethylamine, dipropylamine, diisopropylamine, ethylmethylamine, propylmethylamine, and isopropylmethylamine.

In the case of the single-source system, it is preferred that the other precursors be similar to the aluminum compound of the invention in thermal and/or oxidative decomposition behavior. In the case of a cocktail-source system, it is preferred that the other precursors be similar to the aluminum compound of the invention in thermal and/or oxidative decomposition behavior and, in addition, not alter in properties due to chemical reaction on mixing.

Of the above described other precursors those containing titanium, zirconium, or hafnium include compounds represented by general formulae (II-1) to (II-5):

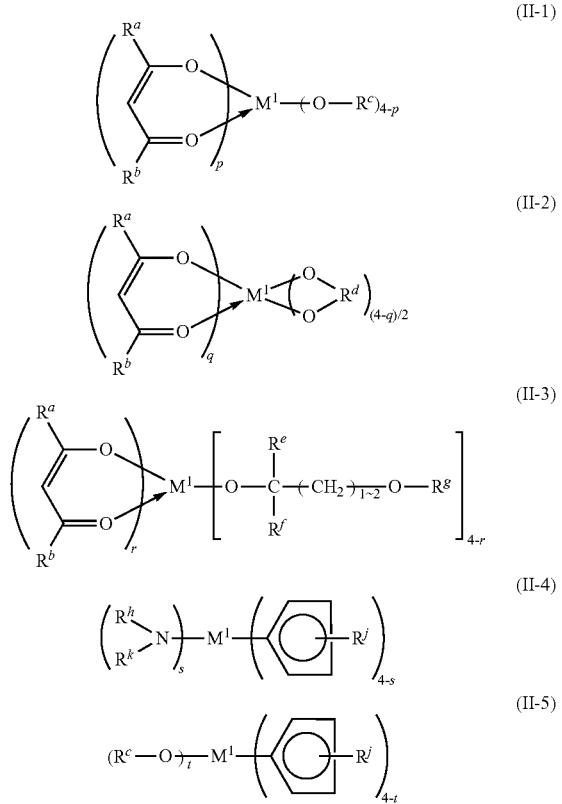

wherein $M^1$ represents titanium, zirconium, or hafnium; $R^a$ and $R^b$ each independently represent a C1-C20 alkyl group optionally substituted with a halogen atom and optionally containing an oxygen atom in its chain; $R^c$ represents a C1-C8 alkyl group; $R^d$ represents an optionally branched C2-C18 alkylene group: $R^e$ and $R^f$ each independently represent a hydrogen atom or a C1-C3 alkyl group; $R^g$, $R^h$, $R^k$, and $R^j$ each independently represent a hydrogen atom or a C1-C4 alkyl group; p represents an integer of 0 to 4; q represents 0 or 2; r represents an integer of 0 to 3; s represents an integer of 0 to 4; and t represents an integer of 1 to 4.

In general formulae (II-1) to (II-5), examples of the C1-C20 alkyl group optionally substituted with a halogen atom and optionally containing an oxygen atom in its chain as represented by $R^a$ and $R^b$ include methyl, ethyl, propyl, isopropyl, butyl, sec-butyl, tert-butyl, isobutyl, amyl, isoamyl, sec-amyl, tert-amyl, hexyl, cyclohexyl, 1-methylcyclohexyl, heptyl, 3-heptyl, isoheptyl, tert-heptyl, n-octyl, isooctyl, tert-octyl, 2-ethylhexyl, trifluoromethyl, perfluorohexyl, 2-methoxyethyl, 2-ethoxyethyl, 2-butoxyethyl, 2-(2-methoxyethoxy)ethyl, 1-methoxy-1,1-dimethylmethyl, 2-methoxy-1,1-dimethylethyl, 2-ethoxy-1,1-dimethylethyl, 2-isopropoxy-1,1-dimethylethyl, 2-butoxy-1,1-dimethylethyl, and 2-(2-methoxyethoxy)-1,1-dimethylethyl. Examples of the C1-C8 alkyl group represented by $R^c$ include methyl, ethyl, propyl, isopropyl, butyl, sec-butyl, tert-butyl, isobutyl, amyl, isoamyl, sec-amyl, tert-amyl, hexyl, 1-ethylpentyl, cyclohexyl, 1-methylcyclohexyl, heptyl, isoheptyl, tert-heptyl, n-octyl, isooctyl, tert-octyl, and 2-ethylhexyl. The optionally branched C2-C18 alkylene group represented by $R^d$ is a group derived from a glycol. Examples of the glycol include 1,2-ethanediol, 1,2-propanediol, 1,3-propanediol, 1,3-butanediol, 2,4-hexanediol, 2,2-dimethyl-1,3-propanediol, 2,2-diethyl-1,3-propanediol, 2,2-diethyl-1,3-butanediol, 2-ethyl-2-butyl-1,3-propanediol, 2,4-pentanediol, 2-methyl-1,3-propanediol, and 1-methyl-2,4-pentanediol. Examples of the C1-C3 alkyl group represented by $R^e$ and $R^f$ include methyl, ethyl, propyl, and 2-propyl. Examples of the C1-C4 alkyl represented by $R^g$, $R^h$, $R^j$, and $R^k$ include methyl, ethyl, propyl, isopropyl, butyl, sec-butyl, tert-butyl, and isobutyl.

Examples of the precursors containing titanium include tetrakisalkoxytitaniums, such as tetrakis(ethoxy)titanium, tetrakis(2-propoxy)titanium, tetrakis(butoxy)titanium, tetrakis(sec-butoxy)titanium, tetrakis(isobutoxy)titanium, tetrakis(tert-butoxy)titanium, tetrakis(tert-amyl)titanium, and tetrakis(1-methoxy-2-methyl-2-propoxy)titanium; tetrakis(β-diketonato)titaniums, such as tetrakis(pentane-2,4-dionato)titanium, (2,6-dimethylheptane-3,5-dionato)titanium, and tetrakis(2,2,6,6-tetramethylheptane-3,5-dionato)titanium; bis(alkoxy)bis(β-diketonato)titaniums, such as bis(methoxy)bis(pentane-2,4-dionato)titanium, bis(ethoxy)bis(pentane-2,4-dionato)titanium, bis(tert-butoxy)bis(pentane-2,4-dionato)titanium, bis(methoxy)bis(2,6-dimethylheptane-3,5-dionato)titanium, bis(ethoxy)bis(2,6-dimethylheptane-3,5-dionato)titanium, bis(2-propoxy)bis(2,6-dimethylheptane-3,5-dionato)titanium, bis(tert-butoxy)bis(2,6-dimethylheptane-3,5-dionato)titanium, bis(tert-amyloxy)bis(2,6-dimethylheptane-3,5-dionato)titanium, bis(methoxy)bis(2,2,6,6-tetramethylheptane-3,5-dionato)titanium, bis(ethoxy)bis(2,2,6,6-tetramethylheptane-3,5-dionato)titanium, bis(2-propoxy)bis(2,6,6,6-tetramethylheptane-3,5-dionato)titanium, bis(tert-butoxy)bis(2,2,6,6-tetramethylheptane-3,5-dionato)titanium, and bis(tert-amyloxy)bis(2,2,6,6-tetramethylheptane-3,5-dionato)titanium; glycoxybis(β-diketonato)titaniums, such as (2-methylpentanedioxy)bis(2,2,6,6-tetramethylheptane-3,5-dionato)titanium and (2-methylpentanedioxy)bis(2,6-dimethylheptane-3,5-dionato)titanium; cyclopentadienyl)tris(dialkylamino)titaniums, such as (methylcyclopentadienyl)tris(dimethylamino)titanium, (ethylcyclopentadienyl)tris(dimethylamino)titanium, (cyclopentadienyl)tris(dimethylamino)titanium, (methylcyclopentadienyl)tris(ethylmethylamino)titanium, (ethylcyclopentadienyl)tris(ethylmethylamino)titanium, (cyclopentadienyl)tris(ethylmethylamino)titanium, (methylcyclopentadienyl)tris(diethylamino)titanium, (ethylcyclopentadienyl)tris(diethylamino)titanium, and (cyclopentadienyl)tris(diethylamino)titanium; and (cyclopentadienyl)tris(alkoxy)titaniums, such as (cyclopentadienyl)tris(methoxy)titanium, (methylcyclopentadienyl)tris(methoxy)titanium, (ethylcyclopentadienyl)tris(methoxy)titanium, (propylcyclopentadienyl)tris(methoxy)titanium, (isopropylcyclopentadienyl)tris(methoxy)titanium, (butylcyclopentadienyl)tris(methoxy)titanium, (isobutylcyclopentadienyl)tris(methoxy)titanium, and (tert-butylcyclopentadienyl)tris(methoxy)titanium.

Examples of the precursors containing zirconium or precursors containing hafnium include the above-listed titanium precursors with titanium displaced with zirconium or hafnium.

Examples of the precursors containing a rare earth element include compounds represented by general formulae (III-1) to (III-3):

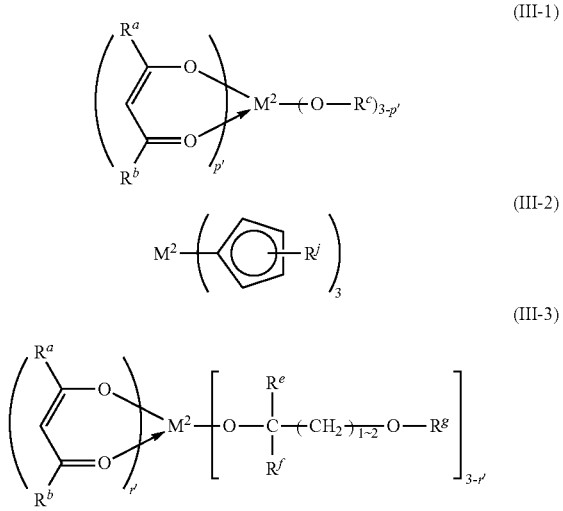

wherein $M^2$ represents a rare earth element; $R^a$ and $R^b$ each independently represent a C1-C20 alkyl group optionally substituted with a halogen atom and optionally containing an oxygen atom in its chain; $R^c$ represents a C1-C8 alkyl group; $R^e$ and $R^f$ each independently represent a hydrogen atom or a C1-C3 alkyl group; $R^g$ and $R^j$ each independently represent a C1-C4 alkyl group; p' represents an integer of 0 to 3; and r' represents an integer of 0 to 2.

Examples of the rare earth element represented by $M^2$ in general formulae (III-1) to (III-3) include scandium, yttrium, lanthanum, cerium, praseodymium, promethium, samarium, europium, gadolinium, terbium, dysprosium, holmium, erbium, thulium, ytterbium, and lutetium. Examples of the groups represented by $R^a$, $R^b$, $R^c$, $R^e$, $R^f$, $R^g$, and $R^j$ include those enumerated for the titanium-containing precursors.

If desired, the thin film forming material of the invention may contain a nucleophilic reagent to stabilize the aluminum compound of the invention and other precursors. Examples of the nucleophilic reagent include ethylene glycol ethers, such as glyme, diglyme, triglyme, and tetraglyme; crown ethers, such as 18-crown-6, dicyclohexyl-18-crown-6, 24-crown-8, dicyclohexyl-24-crown-8, and dibenzo-24-crown-8; polyamines, such as ethylenediamine, N,N'-tetramethylethylenediamine, diethylenetriamine, triethylenetetramine, tetraethylenepentamine, pentaethylenehexamine, 1,1,4,7,7-pentamethyldiethylenetriamine, 1,1,4,7,10,10-hexamethyltriethylenetetramine, and triethoxytriethyleneamine; cyclic polyamines, such as cyclam and cyclen; heterocyclic compounds, such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane; β-keto esters, such as methyl acetoacetate, ethyl acetoacetate, and 2-methoxyethyl acetoacetate; and β-diketones, such as acetylacetone, 2,4-hexanedione, 2,4-heptanedione, and 3,5-heptanedione. The nucleophilic reagent is used usually in an amount of 0.1 to 10 mol, preferably 1 to 4 mol, per mole of the precursor(s).

The thin film forming material of the invention should have minimized contents of impurities other than the constituent components, including impurity metal elements, impurity halogens (e.g., impurity chlorine), and impurity organic matter. The impurity metal element content is preferably 100 ppb or less, more preferably 10 ppb or less, for every element, and a total impurity metal content is preferably 1 ppm or less, more preferably 100 ppb or less. In particular, in the fabrication of a thin film for use as a gate insulator film, a gate film, or a barrier film of LSI devices, it is required to minimize the contents of alkali metal elements, alkaline earth metal elements, and congeneric elements that are influential on the electrical characteristics of the resulting thin film. The impurity halogen content is preferably 100 ppm or less, more preferably 10 ppm or less, even more preferably 1 ppm or less. The total impurity organic matter content is preferably 500 ppm or less, more preferably 50 ppm or less, even more preferably 10 ppm or less. A water content causes particle generation in the chemical vapor deposition material or during thin film formation. Therefore, it is advisable to previously remove the water content from the precursors, the organic solvent, and the nucleophilic reagent as much as possible before use. The water content of each of the precursors, organic solvent, and nucleophilic reagent is preferably 10 ppm or less, more preferably 1 ppm or less.

In order to reduce or prevent contamination of a thin film with particles, it is desirable for the thin film forming material of the invention to have minimized particles. Specifically, it is desirable for the material to have not more than 100 particles greater than 0.3 μm, more desirably not more than 1000 particles greater than 0.2 μm, even more desirably not more than 100 particles greater than 0.2 μm, per ml of its liquid phase as measured with a light scattering particle sensor for detecting particles in a liquid phase.

The process for forming a thin film according to the present invention, which is characterized by using the above described thin film forming material of the invention, comprises vaporizing the aluminum compound of the invention and, if necessary, other precursors, introducing the vapor and, if necessary, a reactive gas to a deposition chamber having a substrate placed therein, and causing the precursor to decompose and/or chemically react to grow and deposit a thin film on the substrate. The process is not particularly restricted by the material delivery system, the mode of deposition, the film formation conditions and equipment, and the like. Any conditions and methods commonly known in the art may be used.

Examples of the reactive gas that may be used if necessary include oxidizing gases, such as oxygen, ozone, nitrogen dioxide, nitrogen monoxide, water vapor, hydrogen peroxide, formic acid, acetic acid, and acetic anhydride; and reducing gases, such as hydrogen. Reactive gases that can be used to form a nitride film include organic amine compounds, such as monoalkylamines, dialkylamines, trialkylamines, and alkylenediamines; hydrazine and ammonia. One or more types of gases may be used.

The material delivery systems include the above-described vapor delivery system, liquid delivery system, single source system, and cocktail-source system.

The deposition modes include thermal CVD (only heat is used to cause the vaporized material or the vaporized material and a reactive gas to react to deposit a film), plasma-enhanced CVD (heat and plasma are used), photo-assisted CVD (heat and light are used), photo plasma-assisted CVD (heat, light, and plasma are used), and ALD in which a deposition reaction of CVD is divided into elementary reaction steps so as to build up a film stepwise on a molecular level.

Examples of the material of the substrate include silicone; ceramics, such as silicon nitride, titanium nitride, tantalum nitride, titanium oxide, titanium nitride, ruthenium oxide, zirconium oxide, hafnium oxide, and lanthanum oxide; glass; and metals, such as metallic ruthenium. The substrate may be platy, spherical, fibrous, or flaky and may have a flat surface or a three-dimensional surface, such as a trench structure.

The film formation conditions as referred to above include reaction temperature (substrate temperature), reaction pressure, and deposition rate. The reaction temperature is preferably 100° C. or higher at which the aluminum compound of the invention and other reactants react sufficiently, more preferably 150° to 400° C. The reaction pressure is preferably from atmospheric pressure to 10 Pa for thermal CVD and photo-assisted CVD or from 10 to 2000 Pa for film formation using plasma. The deposition rate can be controlled by the material feed conditions (vaporizing temperature and vaporizing pressure) and the reaction temperature and pressure. Too high a deposition rate tends to result in deteriorated characteristics of the resulting thin film, and too low a deposition rate can result in poor productivity. A preferred deposition rate ranges from 0.01 to 100 nm/min, more preferably 1 to 50 nm/min. In the case of ALD, the film thickness is controlled by the number of cycles to reach a desired film thickness.

Formation of, for example, an aluminum oxide thin film by an ALD process is carried out as follows. The thin film forming material is vaporized and pulsed (introduced) into a deposition chamber (deposition reaction unit) by the above-described source delivery system (pulse step). Then, a precursor monolayer is formed by the pulsed aluminum compound on the substrate (precursor monolayer formation step). During the precursor monolayer formation step, heat may be applied by heating the substrate or the deposition chamber. The precursor monolayer formed in this step is an aluminum oxide thin film or a thin film formed by the decomposition and/or reaction of part of the aluminum compound and is different in composition from the desired aluminum oxide thin film. The substrate temperature in this step is preferably room temperature to 500° C.

The unreacted aluminum compound gas and by-produced gas are purged out of the deposition chamber (purging step). Although it is ideal for the unreacted aluminum compound gas and by-produced gas to be purged out completely, they do not always have to be. The purging may be achieved by, for example, purging the chamber with an inert gas, such as nitrogen, helium, or argon; evacuating the chamber by reducing the inner pressure; or a combination thereof. The degree of vacuum to be reached by the evacuation is preferably 0.01 to 300 Pa, more preferably 0.01 to 100 Pa.

An oxidizing gas is then pulsed into the chamber and reacts with the precursor monolayer (thin film) with or without heat application to form a monolayer of the desired aluminum oxide (aluminum oxide monolayer formation step). The temperature of the heat, if applied in this step, is preferably room temperature to 500° C., more preferably 150° to 500° C. The aluminum compound of the invention exhibits good reactivity with an oxidizing gas to form an aluminum oxide thin film.

In the case of using an ALD process to form a thin film, the above described series of pulse step, precursor monolayer formation step, purging step, and aluminum oxide monolayer formation step makes one growth cycle, which may be repeated as long as a desired film thickness is reached. In that case, it is preferred that every cycle be followed by purging the unreacted aluminum compound gas and oxidizing gas and the by-produced gas out of the deposition chamber.

In carrying out aluminum oxide thin film formation by ALD, energy such as plasma, light, or electricity may be applied. The stage of energy application is not particularly limited. The energy may be applied at the time of introducing the aluminum compound gas in the pulse step, at the time of heating in the precursor monolayer formation step or the aluminum oxide monolayer formation step, at the time of purging the chamber in the purging step, at the time of introducing the oxidizing gas in the aluminum oxide monolayer formation step, or between any two of the steps.

In the film formation process of the invention, the resulting thin film may be subjected to annealing in an inert atmosphere, an oxidative atmosphere, or a reducing atmosphere to obtain improved electrical characteristics. Where step coverage is required, the process may include the step of reflowing the thin film. The temperature for reflowing is usually from 200° to 1000° C., preferably 250° to 500° C.

Known equipment for chemical vapor deposition can be used to carry out thin film formation using the thin film forming material of the invention. Examples of useful equipment include an apparatus capable of introducing a precursor by a bubbler delivery system as illustrated in FIG. 1, an apparatus having a vaporization chamber as illustrated in FIG. 2, and an apparatus capable of treating a reactive gas with plasma as illustrated in FIGS. 3 and 4. Not only single-substrate type apparatuses like those shown in FIGS. 1 through 4 but batch type apparatuses capable of treating a plurality of substrates in a single chamber are also used.

Combined with appropriate selections of other precursors, a reactive gas, and film forming conditions, the thin film forming material of the invention provides a thin film of desired kind, such as metals, oxide ceramics, nitride ceramics, and glass. The thin films produced by the invention include an aluminum thin film, an aluminum nitride thin film, an aluminum oxide thin film, and a double or complex aluminum oxide thin film. Examples of the double or complex aluminum oxide are $AlSi_xO_y$, $ZrAl_xSiO_y$, $TiAl_xSiO_y$, and $HfAl_xSiO_y$, wherein x and y are selected appropriately with no particular restriction, such as $AlSi_{0.8-1.2}O_{3.1-3.9}$, $ZrAl_2SiO_7$, $TiAl_2SiO_7$, $HfAl_2SiO_7$. These thin films are widely used as LSI wiring materials; hard coatings for mechanical parts and tools; an insulator film, a gate insulator, and a dielectric film of semiconductor memories; electronic components, such as a hard disk MR head; optical glass for optical communication circuits; and catalysts.

EXAMPLES

The present invention will now be illustrated in greater detail with reference to Examples and Evaluation Examples, but it should be understood that the invention is not construed as being limited thereto.

Example 1

Preparation of Compound No. 1

In an argon atmosphere, 15.2 g of aluminum (III) chloride and 38.6 g of dehydrated hexane were put in a reaction flask and stirred in a water cooling bath. To the mixture was added dropwise 25.3 g of ethylmethylamine, followed by stirring for 2 hours. The mixture was cooled in an ice-cooling bath to 15° C., and 150.2 g of a 1.6 mol/l hexane solution of n-butyl lithium was added thereto dropwise. After the addition, the reaction system was allowed to warm to room temperature and stirred for about 16 hours. Subsequently, 11.9 g of N,N,N'-trimethylethylenediamine was added dropwise, and the mixture was stirred for about 20 hours, followed by filtration. Hexane was removed from the filtrate, and the liquid residue was distilled under a reduced pressure of 40 Pa at a bath temperature of 105° C. A distillate was collected at a tower top temperature of 65° C. The recovery by this purification was 57%. The resulting compound was a pale yellow liquid, which was identified to be compound No. 1 as a result of elemental analysis and $^1$H-NMR analysis. These analytical results are shown below together with the results of TG-DTA.

Analytical Results:

(1) Metal elemental analysis by ICP-AES

Al 11.1 mass % (theo.: 11.04 mass %); C, 50.17 mass %; H, 11.45 mass %; N, 22.61 mass % (theo.: C, 54.07 mass %; H, 11.96 mass %; N, 22.93 mass %)

(2) $^1$H-NMR (solvent: deuterobenzene) (chemical shift, multiplicity, number of protons) (1.239 ppm, t, 6), (1.778 ppm, s, 6), (2.161 ppm, t, 2), (2.704 ppm, t, 2), (2.796 ppm, s, 6), (2.832 ppm, s, 3), (3.029 ppm, m, 2), (3.182 ppm, m, 2)

(3) TG-DTA (Ar: 100 ml/min; temperature rise: 10° C./min; amount of sample: 9.543 mg)

Fifty percent mass loss temperature: 170° C.

Example 2

Preparation of Compound No. 2

In an argon atmosphere, 5.3 g of aluminum (III) chloride, 10.1 g of dehydrated hexane, and 14.2 g of tetrahydrofuran were put in a reaction flask and stirred in a water cooling bath. To the mixture was added dropwise 12.2 g of isopropylmethylamine, followed by stirring for 1 hour. The mixture was cooled in an ice-cooling bath to 5° C., and 52.5 g of a 1.6 mol/l hexane solution of n-butyl lithium was added thereto dropwise. After the addition, the reaction system was allowed to warm to room temperature and stirred for about 2 hours. Subsequently, 4.2 g of N,N,N'-trimethylethylenediamine was added dropwise, and the mixture was stirred for about 13 hours, followed by filtration. Hexane and tetrahydrofuran was removed from the filtrate, and the liquid residue was distilled under a reduced pressure of 40 Pa at a bath temperature of 115° C. A distillate was collected at a tower top temperature of 75° C. The recovery by this purification was 45%. The resulting compound was a pale yellow liquid, which was identified to be compound No. 2 as a result of elemental analysis and $^1$H-NMR analysis. These analytical results are shown below together with the results of TG-DTA.

Analytical Results:

(1) Metal elemental analysis by ICP-AES

Al 9.98 mass % (theo.: 9.90 mass %); C, 54.82 mass %; H, 11.59 mass %; N, 20.24 mass % (theo.: C, 57.32 mass %; H, 12.21 mass %; N, 20.57 mass %)

(2) $^1$H-NMR (solvent: deuterobenzene) (chemical shift, multiplicity, number of protons) (1.299 ppm, d, 6), (1.306 ppm, d, 6), (1.817 ppm, s, 6), (2.200 ppm, t, 2), (2.658 ppm, s, 6), (2.698 ppm, t, 2), (2.817 ppm, s, 3), (3.478 ppm, m, 2)

(3) TG-DTA (Ar: 100 ml/min; temperature rise: 10° C./min; amount of sample: 9.903 mg)

Fifty percent mass loss temperature: 180° C.

Evaluation Example 1

Evaluation of Pyrophoricity of Aluminum Compound

The aluminum compound Nos. 1 and 2 of the invention and Comparative Compounds 1 to 3 shown below were examined for pyrophoricity in air. Specifically, a compound that ignited in one hour standing in the atmosphere was rated "pyrophoric (yes)", and a compound that did not ignite in one our standing in the atmosphere was rated "nonpyrophoric (no)". The results are shown in Table 1 below.

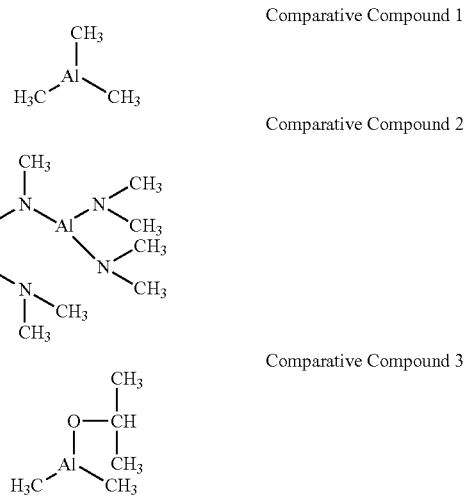

TABLE 1

| Compound | Pyrophoricity |
|---|---|
| Comparative Compound 1 | yes |
| Comparative Compound 2 | no |
| Comparative Compound 3 | no |
| Compound No. 1 | no |
| Compound No. 2 | no |

The results in Table 1 prove that Comparative Compound 1 has pyrophoricity in the atmosphere. A pyrophoric compound is difficult to handle as a material for chemical vapor deposition from the standpoint of safety. The aluminum compounds of the invention (compound Nos. 1 and 2) and Comparative Compounds 2 and 3 were proved nonpyrophoric and safely usable in the atmosphere.

Evaluation Example 2

Evaluation of Thermal Stability of Aluminum Compound

Thermal stability of the aluminum compound Nos. 1 and 2 of the invention and Comparative Compounds 2 and 3 was evaluated by measuring the temperature at which thermal decomposition occurs using a differential scanning calorimeter. The results obtained are shown in Table 2 below.

TABLE 1

| Compound | Thermal Decomposition Onset Temperature (° C.) |
|---|---|
| Comparative Compound 2 | 300 |
| Comparative Compound 3 | 190 |
| Compound No. 1 | 330 |
| Compound No. 2 | 330 |

The results in Table 2 reveal that the aluminum compound Nos. 1 and 2 of the invention exhibit higher thermal stability by about 30° C. than Comparative Compound 2. The aluminum compound Nos. 1 and 2 of the invention exhibit higher thermal stability by about 140° C. than Comparative Compound 3. Compounds having high thermal stability are superior for use as a material for chemical vapor deposition because film formation can be performed at a high temperature to provide a high quality thin film.

Evaluation Example 3

Evaluation of Physical Properties of Aluminum Compound

The state of the aluminum compound Nos. 1 and 2 of the invention and Comparative Compound 2 was observed with the naked eye at 10° C. under ambient pressure. The viscosity of each compound at 25° C. under ambient pressure was measured using AMVn Automated Microviscometer from Anton Paar.

TABLE 3

| Compound | State (10° C.) | Viscosity (25° C.) |
|---|---|---|
| Comparative Compound 2 | solid | 10.2 cps |
| Compound No. 1 | liquid | 8.8 cps |
| Compound No. 2 | liquid | 12.9 cps |

It can be seen from the results in Table 3 that aluminum compound Nos. 1 and 2 of the invention are low-melting compounds that were liquid under the condition of 10° C., while Comparative Compound 2 was solid at 10° C. It is also seen that compound No. 1, in particular, has a lower viscosity at 25° C. than Comparative Compound 2. Low-melting compounds are advantageous for use as a material of chemical vapor deposition because of stable transportability in a liquid state and, in particular, one having a low viscosity is especially advantageous for ease of transportation.

Example 3

Formation of Aluminum Oxide Thin Film by ALD

An aluminum oxide thin film was formed on a silicon wafer substrate by ALD using compound No. 1 as a material for chemical vapor deposition and the apparatus illustrated in FIG. 1 under the following conditions. The thickness of the resulting thin film was measured by X-ray reflectometry, and the structure and composition of the thin film were confirmed by X-ray diffractometry and X-ray photo electron spectroscopy. As a result, the film thickness was 4.1 nm, and the film composition was aluminum oxide ($Al_2O_3$) with a carbon content below the detection limit of 0.1 atom %. The film thickness per cycle was 0.08 to 0.09 nm.

Conditions:
  Reaction temperature (substrate temperature): 260-420° C.
  Reactive gas: ozone gas
Steps:
  Fifty cycles each comprising steps (1) to (4) were conducted.
  (1) The chemical vapor deposition material vaporized under conditions of a material container temperature of 23° C. (room temprature) and a material container inner pressure of 80 Pa was pulsed into the deposition chamber and deposited on the substrate for 10 seconds under a system pressure of 80 Pa.
  (2) The chamber was purged with argon for 15 seconds to remove the unreacted material.
  (3) The reactive gas was pulsed into the deposition chamber and allowed to react with the deposit formed in the step (1) for 10 seconds under a system pressure of 80 Pa.
  (4) The deposition chamber was purged with argon for 5 seconds to remove the unreacted material from the chamber.

Example 4

Formation of Aluminum Oxide Thin Film by ALD

An aluminum oxide thin film was formed on a silicon wafer substrate by ALD using compound No. 2 as a material for chemical vapor deposition and the apparatus illustrated in FIG. 1 under the following conditions. The thickness of the resulting thin film was measured by X-ray reflectometry, and the structure and composition of the thin film were confirmed by X-ray photo electron spectroscopy. As a result, the film thickness was 3.1 nm; the film composition was aluminum oxide ($Al_2O_3$) with a carbon content of 0.2 atom %. The film thickness per cycle was 0.06 nm.

Conditions:
  Reaction temperature (substrate temperature): 260-420° C.
  Reactive gas: ozone gas
Steps:
  Fifty cycles each comprising steps (1) to (4) were conducted.
  (1) The chemical vapor deposition material vaporized under conditions of a material container temperature of 45° C. and a material container inner pressure of 80 Pa was pulsed into the deposition chamber and deposited on the substrate for 10 seconds under a system pressure of 80 Pa.
  (2) The chamber was purged with argon for 15 seconds to remove the unreacted material.
  (3) The reactive gas was pulsed into the deposition chamber and allowed to react with the deposit formed in the step (1) for 10 seconds under a system pressure of 80 Pa.
  (4) The deposition chamber was purged with argon for 15 seconds to remove the unreacted material from the chamber.

The invention claimed is:
1. A method for producing a thin film, the method comprising:
  introducing, into a deposition chamber in which a substrate is placed, a vapor that has been obtained by vaporizing a material for thin film formation comprising an aluminum compound represented by general formula (I):

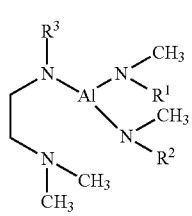 (I)

wherein $R^1$ and $R^2$ each independently represent a branched alkyl group having 3 to 5 carbon atoms, and $R^3$ represents a methyl group or an ethyl group; and forming an aluminum-containing thin film on a surface of the substrate by decomposing and/or chemical reacting the aluminum compound.

2. The method according to claim 1, wherein $R^1$ and $R^2$ each independently represent an isopropyl group, a tert-butyl group or a tert-pentyl group.

3. The method according to claim 1, wherein $R^1$ and $R^2$ each independently represent an isopropyl group or a tert-butyl group.

4. The method according to claim 1, wherein $R^1$ and $R^2$ each represent an isopropyl group.

* * * * *